United States Patent [19]

Santangelo et al.

[11] Patent Number: 4,604,089
[45] Date of Patent: Aug. 5, 1986

[54] PRESSURE REGULATED IRRIGATION SYSTEM FOR ARTHROSCOPY

[75] Inventors: John A. Santangelo, East Freetown; Charles B. Worrick, III, Hanson, both of Mass.

[73] Assignee: Codman & Shurtleff, Inc., Randolph, Mass.

[21] Appl. No.: 523,312

[22] Filed: Aug. 15, 1983

[51] Int. Cl.⁴ .................... F16K 1504; A61B 17/32
[52] U.S. Cl. ...................... 604/30; 128/DIG. 12; 604/5; 604/35; 604/118
[58] Field of Search ............... 128/DIG. 12; 604/5, 604/6, 27, 29, 30, 22, 28, 31, 34, 35, 65, 118; 251/45, 61.1; 137/487, 492, 510

[56] References Cited

U.S. PATENT DOCUMENTS

| | | | |
|---|---|---|---|
| 3,110,469 | 11/1963 | Becker | 251/45 |
| 3,429,313 | 2/1969 | Romanelli | 604/35 |
| 3,604,419 | 9/1971 | Diskin | 128/DIG. 13 |
| 3,830,234 | 8/1974 | Kopp | 604/30 |
| 4,117,843 | 10/1978 | Banko | 604/65 |
| 4,184,510 | 1/1980 | Murry et al. | 604/30 |
| 4,237,879 | 12/1980 | Genese | 604/81 |
| 4,411,792 | 10/1983 | Babb | 604/30 |
| 4,490,135 | 12/1984 | Troutner | 128/DIG. 13 |

Primary Examiner—Stephen C. Pellegrino
Assistant Examiner—Mark Rooney
Attorney, Agent, or Firm—Donal B. Tobin

[57] ABSTRACT

A pressure regulated system for an irrigation system including a reservoir of irrigation fluid, a pump, catheters for providing access to and egress from the irrigation site and a pressure regulation circuit, all connected in series with one another. The pressure regulation circuit includes a flow restriction branch having a normally-open valve and a variable orifice, diaphragm-operated, restrictor and a pressure accumulation branch, having a check valve, accumulator, and a normally-closed valve. A conduit running from the pressure accumulation branch to the diaphragm controls the pressure regulator. The operator may raise the pressure by closing the normally-open valve to direct pump flow to the pressure accumulation branch and thereby restrict the orifice of the pressure regulator until the desired pressure has been reached, and then releases the valve to maintain that pressure. To reduce the pressure, one opens the normally-closed valve to vent the pressure accumulation branch and reduce the pressure in the diaphragm of the pressure regulator.

18 Claims, 3 Drawing Figures

PRESSURE REGULATED IRRIGATION SYSTEM FOR ARTHROSCOPY

FIELD OF THE INVENTION

The present invention relates to an apparatus for controlling the pressure of an irrigation fluid introduced into an arthroscopy site from a traditional saline reservoir without raising or lowering the reservoir.

BACKGROUND OF THE INVENTION

When conducting arthroscopy surgery, for example in removing cartilage from a knee joint or other joint of the body, surgeons often introduce fluid under pressure into the joint to expand the joint so that it may be worked on more easily and to provide a fluid flow for flushing debris from the joint. This is usually done by elevating a bottle of saline solution on a well-known, vertically adjustable intravenous infusion stand and connecting a fluid line to a catheter inserted into the joint. The flow from the joint can be through an additional catheter attached to a collection bag. Pressure of the fluid introduced to the joint can be increased or decreased by raising or lowering the saline reservoir on the vertically adjustable intravenous stand.

It would be desirable to have an apparatus which could be used to raise and lower the pressure of the fluid in the joint without having to go through the sometimes awkward procedure of raising and lowering the saline reservoir. It would also be desirable to have a pressure regulated system in which the irrigation fluid could be filtered, clarified, sterilized and recirculated through the irrigation site.

SUMMARY OF THE INVENTION

The present invention provides an apparatus for raising and lowering the pressure in the arthroscopy operative (or any other relatively sealed operative site which could be subjected to a pressurized flow) without adjusting the height of the saline reservoir on the intravenous stand. It is preferably a closed system through which the irrigation fluid can be recirculated, but it can also function as a nonrecirculating system. The apparatus used in the pressure-regulated irrigation system includes devices for providing access to and egress from the irrigation site. These can be catheters or other types of devices, e.g., instruments, introduced to the operative site through the surrounding tissue. When the catheter is introduced through the skin, the surrounding tissue tends to close around the exterior of the catheter to provide a seal. This system also includes a reservoir of irrigation fluid and a pump (preferably a vacuum operated pump) which can be connected to the irrigation site, for example by standard intravenous tubing. The tubing provides a tight seal with the catheters to avoid leakage. A pressure-regulation circuit is connected into the fluid system in series with the pump and the reservoir. The pressure regulation circuit permits the operator to actuate a first control to elevate the pressure in the irrigation site to a desired level and to maintain the pressure at that desired level when the first control is deactivated. The pressure regulation circuit also permits the operator to actuate a second control to reduce the pressure at the irrigation site to a base level determined by the height of the reservoir and to maintain the pressure at that reduced level when the second control is deactivated.

In its preferred embodiment, the pressure-regulation circuit is connected in series with the pump and includes a flow restriction branch having a normally-open valve connected in series with a variable pressure regulator. The pressure-regulation circuit also includes a pressure accumulation branch connected in parallel with the flow restriction branch and having a check valve, (to permit flow only in one direction from the injection site into the pressure accumulation branch), an accumulator and a normally-closed valve. The check valve, accumulator and the normally-closed valve are all connected in series with each other. The downstream portion of the normally-closed valve connects with the downstream portion of the flow restriction branch downstream of the pressure regulator. Also in the preferred embodiment, the pressure regulator is a diaphragm-operated, variable orifice, pressure regulator. There is a pressure line connected between the pressure accumulation branch and the diaphragm of the variable orifice pressure regulator for varying the pressure regulator.

This flow regulation circuit permits an operator to close the normally-open valve and to direct fluid under the influence of the pump into the pressure accumulation branch of the circuit where flow is accumulated for as long as the normally-open valve is closed. When the normally-open valve is open, flow resumes through the flow restriction branch and through the pressure regulator back to the input side of the pump. The pressure accumulated in the pressure accumulation branch of the circuit is communicated through a fluid pressure line to the diaphragm of the variable orifice, diaphgram-operated pressure regulator. Thus, as the pressure in the pressure accumulation branch is increased, the orifice of the pressure regulator is decreased to increase the pressure in the irrigation site. If the operator wishes to reduce the pressure, the operator merely actuates the normally-closed valve which relieves the pressure in the pressure accumulation branch of the pressure regulation circuit and permits it to drop as long as the normally-closed valve is kept open. As soon as the normally-closed valve is permitted to close again, the pressure will stay at the level that then remains in the pressure accumulation branch.

Thus it can be seen that the operator, merely by operating two valves, can automatically raise or lower the pressure in the irrigation site, and there is no need to go through the sometimes awkward practice of raising and lowering a saline reservoir on a traditional intravenous stand.

The entire pressure regulated irrigation system can be inexpensively made and completely disposable.

An injection site may be included in the system upstream of the irrigation site for introducing medicament into the irrigation site.

A filter can be included in series with the irrigation site for removing and capturing for subsequent analysis debris which is flushed from the irrigation site during any operative procedures for which this circuit is used. The filter may be chosen to filter bacteria and blood from the flow to sterilize and clarify the fluid.

The pump is preferably a vacuum-driven pump but may also be a pneumatic pressure-operated pump which can be operated by ordinary vacuum or pressure sources available in the operating room. It could also be a liquid-operated pump. This pump could be either an impeller-operated, constant flow pump or a reciprocating kind of pump. Of course, an electrically operated pump operating off AC line voltage or a DC battery could also be used. However, it is more desirable to eliminate electrically operated devices from the operating room environment.

These and other features and advantages of the present invention will become apparent from the following detailed description of the preferred embodiments taken in conjunction with the following drawings.

BRIEF DESCRIPTION OF THE DRAWINGS

FIG. 1A shows a schematic representation of a component of the system shown in FIG. 1.

DETAILED DESCRIPTION OF THE PREFERRED EMBODIMENT

Figure 1:
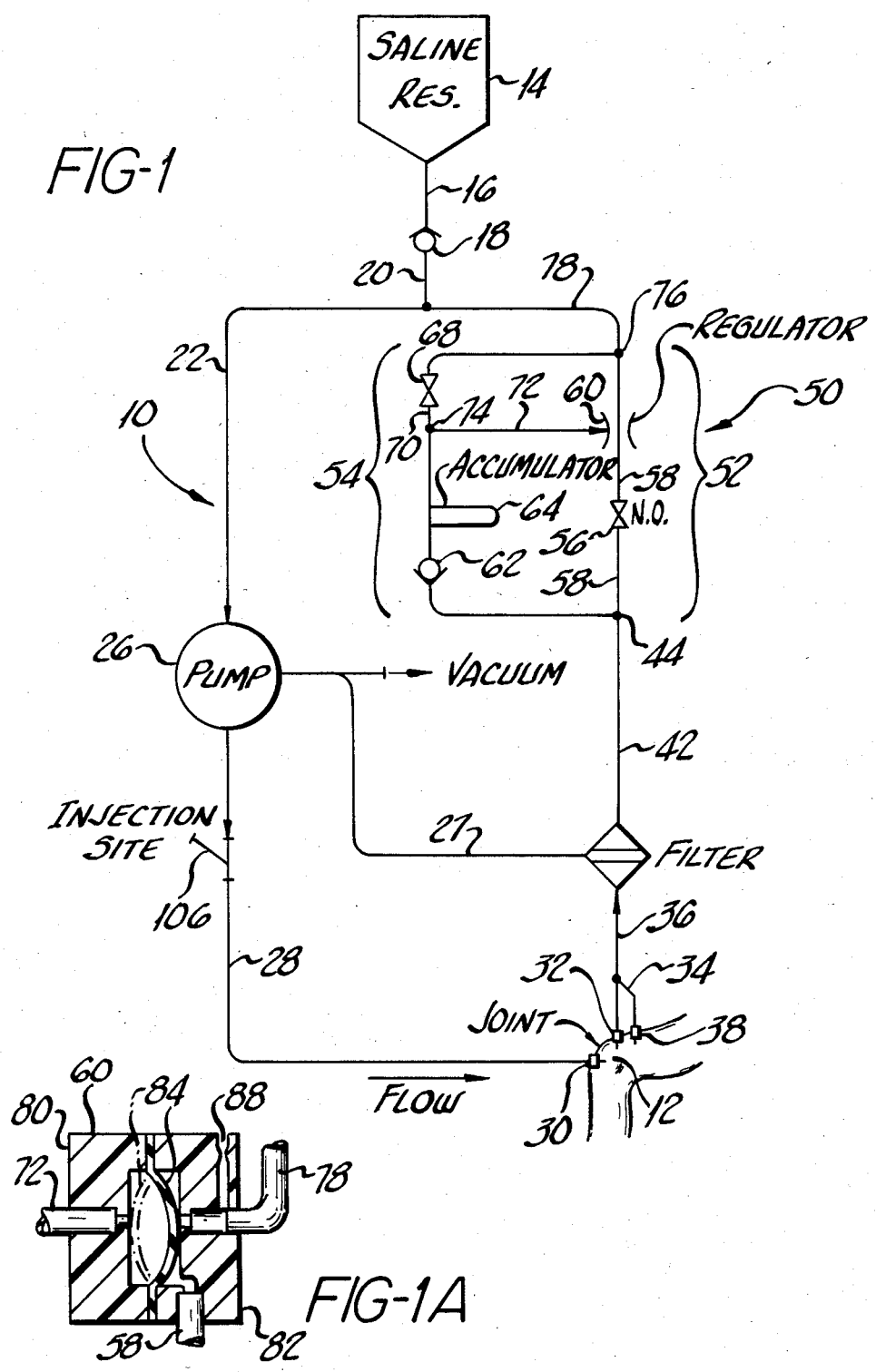
FIG. 1 shows a schematic representation of the pressure regulated irrigation system of the present invention.

Referring now to FIG. 1 there is shown a schematic representation of the pressure regulated irrigation system of the present invention generally designated as 10 and connected to an irrigation site shown in FIG. 1 as the knee joint 12 of a patient upon whom an operation is being conducted. The system of this invention can be used with other joints and may also be used in areas of the body other than joints. A source of irrigation fluid 14, normally a saline solution, supported by any conventional means, for example by hanging the bag on a standard intravenous infusion stand (not shown). Flow is directed from saline reservoir 14 through a fluid conduit 16 through a check valve 18 and a further fluid conduits 20, and 22 to a pump 26. Check valve 18 prevents flow from the system 10 back into the reservoir 14.

Pump 26 is preferably a vacuum-operated pump, but it can also be pneumatic or a liquid-operated pump of either the constant flow impeller variety or the reciprocating variety. Pump 26 could also be an electrically operated pump which operates on normal alternating current line voltage or on direct current battery power. It is preferable to use a vacuum, pneumatic or liquid-operated pump rather than an electrically operated pump in the operating room environment for reasons well known to those skilled in the art. A vacuum line 27 may be connected to pump 26 to provide a source of vacuum to run the pump 26.

Fluid conduit 28 provides connection to the irrigation site through a catheter 30 of well known construction which may be inserted through the tissue surrounding the knee joint into the joint 12. Fluid conduit 28 is tightly connected to catheter 30 to avoid leakage. Tissue contraction around the exterior of catheter 30 provides a relatively leak-resistant entry to joint 12. The surgeon may wish to use additional sealing elements so that a higher pressure may be sustained within the operative site. A second similar catheter 32 provides sealed egress of the irrigation fluid from joint 12.

A connection 34 is provided in conduit 36 downstream of joint 12 and may be used to connect an aspiration port 38 of an operating instrument (not shown) which can be inserted into joint 12.

A filter 40 may be connected to conduit 36 downstream of the irrigation site. Filter 40 may be used to remove debris which is flushed from the irrigation site or to capture the debris for subsequent analysis. Filter 40 can also be used to remove bacteria and, thus, sterilize the fluid in the system or to remove blood and very small particulate debris to clarify the fluid. A vacuum line 27 may be connected to the filter to remove debris that collects in the filter. This can be the same vacuum line that operates pump 26.

A pressure regulation circuit 50 is connected in series with pump 26 and reservoir 14. Conduit 42 connects to input 44 of pressure regulation circuit 50. Pressure regulation circuit 50 has a flow restriction branch 52 and a pressure accumulation branch 54 connected in parallel with one another. Flow restriction branch 52 includes a valve 56. Valve 56 is preferably a normally-open, push-button-operated, spring-return valve. Such a push-button valve could operate to pinch off conduit 58 which forms the flow conduit of flow restriction branch 52. However, any suitable valve could be used, for example a stopcock spliced into line 58. In series with valve 56 is a variable pressure regulator 60 which in the preferred embodiment is a diaphragm-operated, variable-orifice pressure regulator of the type known as a pressure repeator available from Clippard Instrument Laboratories, Inc. of Cincinnati, Ohio, under Part No. 1043, whose structure and function will be described subsequently in this application.

The pressure accumulation branch 54 includes a check valve 62, an accumulator 64 and valve 68 which is preferably a normally-closed, push-button-operated, spring-return valve 68 which, when in its normally-closed position, obstructs fluid flow in pressure accumulation branch 54 but when activated by the operator permits fluid flow through pressure accumulation branch 54. Normally-closed valve 68 is similar in construction to normally-open valve 56 except in its normally-closed position it could pinch the conduit 70 of pressure accumulator branch 54 closed. As with valve 56, alternative valve constructions may be used.

A conduit 72 connects the pressure accumulation branch 54 from a point 74 just upstream of normally-closed valve 68 to the diaphragm of pressure regulator 60. Conduit 72 provides a means for transmitting a signal representative of the pressure in pressure accumulation branch 54 to the variable pressure regulator 60. The downstream connection 76 of pressure regulation circuit 50 is connected by conduit 78 to conduit 22. Check valve 18 prevents any fluid from traveling back up conduit 20 into saline reservoir 14. On the other hand, fluid may flow from saline reservoir 14 into the system 10 to replace any fluid which leaks from the system, particularly at the irrigation site in joint 12 or to increase the volume of fluid in the recirculating loop which includes the joint to expand the joint.

The structure of diaphragm-operated, variable-pressure regulator 60 is shown schematically in FIG. 1A where regulator 60 is shown to include two housings 80 and 82 between the confronting surfaces of which diaphragm 84 is fixed. Housings 80 and 82 define a chamber 86 in fluid communication with control line 72 output 78 and input line 58 of pressure regulation circuit 50. Regulator 60 has a bleed orifice 88. Diaphragm 80 will move left (toward the dotted line position) in FIG. 1A or right to restrict flow into output line 78 depending upon the pressure differential across diaphragm 84. Diaphragm 84 moves to the left or right and acts like a valve to increase or decrease the flow through output 78 and hence the pressure in irrigation site 12.

In operation and still referring to FIG. 1, it can be seen that the pressure in the system 10 can be raised if the operator closes normally-open valve 56 to interrupt the flow in flow restriction branch 52 of pressure regulation circuit 50. Flow will be directed from the pump 26 into pressure accumulator branch 54 of pressure regulation circuit 50 through check valve 62 into accumulator 64. The pressure will continue to build up in pressure accumulation branch 54 until the operator releases normally-open valve 56. When normally-open valve 56 is released, the pressure accumulated in branch 54 will maintain its accumulated level because check valve 62 prevents the accumulated pressure in accumulator 64 from dropping. The accumulated pressure in accumulator 64 is transmitted to the diaphragm of pressure regulator 60 by means of a conduit 72 connected between pressure accumulator branch 54 just upstream of normally-closed valve 68, and the diaphragm section of the variable pressure regulator 60. By transmitting the accumulated pressure from accumulator 64 to the diaphragm section of regulator 60, the variable orifice in regulator 60 restricts so that when normally-open valve 56 is reopened, the position of the variable orifice of variable regulator 60 has been changed to a new value and will be maintained at that value so as to increase pressure in the entire system 10 and particularly at the irrigation site within joint 12.

When the operator wishes to reduce the pressure in the irrigation site in joint 12, one merely pushes the button to open normally-closed valve 68 and relieves the pressure from accumulator 64 to the junction point 76 on the downstream side of pressure regulation circuit 50. When this accumulated pressure is relieved, the conduit 72 connecting the diaphragm of regulator 60 communicates that lower pressure to the diaphragm and permits the variable orifice to open further and reduce the pressure in the flow restriction branch 52 of regulation circuit 50.

Thus, it can be seen that the pressure can be increased and decreased at the irrigation site merely by pushing one button on normally-open valve 56 to increase the pressure and pushing a second button on normally-closed valve 68 to reduce the pressure. The pressure that is set by operating valves 56 and 58 will be maintained at the set level so that the operator need not continue to push the valve once the desired pressure level is reached.

Figure 2:
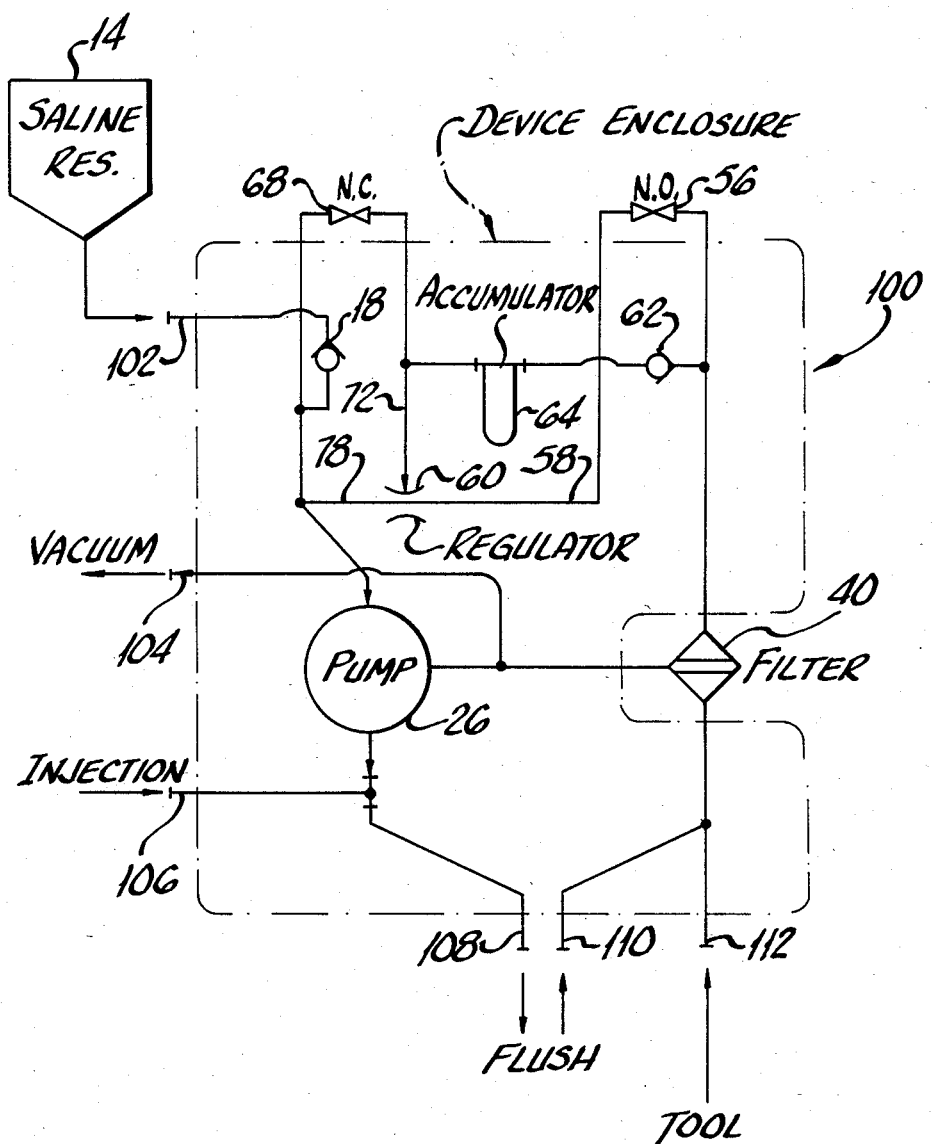
FIG. 2 shows a schematic view of the pressure regulated irrigation system of the present invention arranged in such a way as to be packaged in a single disposable unit adapted for ready connection to other systems used with the circuit, for example a saline reservoir, vacuum source for the filter and for the pump and an injection site.

Referring now to FIG. 2, there is shown, still schematically, a piece of hardware which contains the elements of the fluid system 10 shown in FIG. 1 in a configuration adapted to be connected to the various input requirements for the system. This hardware is contained in a housing 100 and includes connection fittings 102 for connecting a saline reservoir into the housing, a connection fitting 104 for connecting a source of vacuum into the housing for operating the pump 26 and for clearing filter 40, an optional connection fitting 106 for injecting medicament into the pressure regulated irrigation system, fitting 108 for connecting to access catheter 30, fitting 110 for connecting to an egress catheter 32 and fitting 112 for connecting to an aspiration port 38 of an operating tool. The piece of hardware may be a plastic housing 100 defining a cavity in which the elements of system 10 are placed in convenient orientation.

The push button of normally-open valve 56 projects through the wall of housing 100 as does the push button of normally-closed valve 68. This housing and all of its parts may be made of inexpensive plastic and plastic flexible tubing may be woven through the housing according to the schematic diagram shown in FIG. 2 to provide the fluid communication among the various parts of the system. This construction permits the entire housing and all of its parts to be made of inexpensive material so that the entire device may be made as a disposable unit.

As also shown in both FIGS. 1 and 2, an optional injection site 106 may be connected in series downstream of pump 26 on the upstream side of the irrigation site for injecting various medicament into the fluid system.

It will be appreciated that the present invention provides a pressure regulated system for an irrigation site which permits the pressure to be quickly and easily elevated and maintained at the desired elevated level and then equally easily reduced and maintained at the reduced level without the necessity of raising and lowering an irrigation fluid reservoir on a traditional intravenous infusion stand. The present invention has been described in conjunction with preferred embodiments. Those skilled in the art will appreciate that many modifications and changes may be made to the preferred embodiments without departing from the present invention. It is, therefore, not intended to limit the present invention except as set forth in the appended claims.

We claim:

1. A pressure regulated irrigation system comprising:
means for providing access to and egress from the irrigation site;
means in fluid communication with said access and egress means for providing a closed loop fluid circuit about the irrigation site;
means for connecting a reservoir of irrigation fluid into said circuit;
pump means in fluid communication with and connected in series with said reservoir connection means; and,
a pressure regulation circuit in fluid communication with and connected in series with said pump means and said reservoir connection means, said pressure regulation circuit including an operator first input means for elevating the pressure in said irrigation site to a desired level in response to an operator first input signal and for maintaining said pressure at said desired level when said operator first input signal is terminated; and,
said pressure regulation circuit further including an operator second input means for reducing the pressure at said irrigation site in response to an operator second input signal and for maintaining said pressure at said reduced level when said second input signal is terminated;
wherein said pressure regulation circuit includes a flow restriction branch and a pressure accumulation branch connected in parallel with said flow restriction branch;
said flow restriction branch including said operator first input means and a pressure regulator downstream of and connected in series with said operator first input means;
said pressure accumulation branch including said operator second input means, a pressure accumulation means upstream of and connected in series with said operator second input means and a check valve means upstream of and connected in series with said pressure accumulation means; and, means for transmitting a signal representative of the pressure in said pressure accumulation branch to control said pressure regulator in said flow restriction branch.

2. A pressure regulation apparatus for an irrigation system comprising:

a housing defining a cavity;

a pump means having an input and an output and disposed in said housing cavity;

a first fitting in said housing for providing fluid access to the irrigation site from the sytem;

conduit means connected in series between said pump output and said first fitting;

a second fitting in said housing for providing egress from said irrigation site into the system;

a third fitting in said housing for connecting the sytem to a reservoir of irrigation fluid;

conduit means connected in series between said pump inlet and said reservoir;

a fourth fitting in said housing for connecting said pump to a power source for said pump;

pressure regulation circuit means disposed principally within said cavity and connected in series with said pump means between said second fitting and said pump means input;

said pressure regulation circuit including a first flow restriction branch including a valve for interrupting flow in said flow restriction branch and a variable pressure regulator downstream of and connected in series with said flow restriction branch valve;

said flow regulation circuit further including a pressure accumulation branch connected in parallel with said flow restriction branch and including a check valve, an accumulator downstream of and connected in series with said check valve and a second valve downstream of and connected in series with said accumulator for intermittently permitting flow through said pressure accumulation branch;

said first and second valves adapted to project through said housing wall for easy access by an operator; and said pressure regulation circuit further including means for transmitting a signal representative of the pressure in said pressure accumulation branch connected between the downstream side of the accumulator and said variable pressure regulator to control said variable pressure regulator;

whereby an operator may close said first valve to interrupt flow in said flow restriction branch and thereby cause pressure to build up in said pressure accumulation branch to a predetermined level and to be maintained at the predetermined level when the flow interruption valve is released by the operator, said accumulated pressure controlling said pressure regulator and increasing the pressure at the irrigation site; and, further whereby when the operator activates the second valve permitting intermittent flow in said pressure accumulation branch, thus relieving the accumulated pressure and allowing said pressure regulator to decrease the pressure at the irrigation site to a desired level and to stay at that desired level when the operator stops the flow in the pressure accumulation branch.

3. The apparatus of claim 2 wherein said first valve is a normally-open, push-button-operated, spring-return valve.

4. The apparatus of claim 2 wherein said second valve is a normally-closed, push-button-operated, spring-return valve.

5. The apparatus of claim 2 including a filter disposed outside of said housing but adapted for connecting between said second fitting and said pressure regulation circuit.

6. A pressure regulated irrigation system comprising:

means for providing access to and egress from the irrigation site;

means in fluid communication with said access and egress means for providing a closed loop fluid circuit about the irrigation site;

means for connecting a reservoir of irrigation fluid into said circuit;

pump means in fluid communication with and connected in series with said reservoir connection means; and, a pressure regulation circuit in fluid communication with and connected in series with said pump means and said reservoir connection means, said pressure regulation circuit including an operator first input means for elevating the pressure in said irrigation site to a desired level in response to an operator first input signal and for maintaining said pressure at said desired level when said operator first input signal is terminated; and, said pressure regulation circuit further including an operator second input means for reducing the pressure at said irrigation site in response to an operator second input signal and for maintaining said pressure at said reduced level when said second input signal is terminated;

wherein said pressure regulation circuit includes a flow restriction branch and a pressure accumulation branch connected in parallel with said flow restriction branch;

said flow restriction branch including said operator first input means and a pressure regulator downstream of and connected in series with said operator first input means;

said pressure accumulation branch including said operator second input means, a pressure accumulation means upstream of and connected in series with said operator second input means and a check valve means upstream of and connected in series with said pressure accumulation means;

means for transmitting a signal representative of the pressure in said pressure accumulation branch to control said pressure regulator in said flow restriction branch; and, said pressure regulator including a diaphragm-operated pressure regulator and said means for transmitting a signal representative of the pressure in said pressure accumulation branch including a conduit connected to the donwstream side of said pressure accumulator and in fluid communication with said diaphragm of said diaphragm-operated pressure regulator.

7. The system of claim 6 wherein said means for providing access to the irrigation site includes a catheter introduced to the irrigation site through surrounding tissue and said means for providing egress from the irrigation site includes a second catheter introduced into the irrigation site through the surrounding tissue.

8. The system of claim 6 wherein said pump means includes a vacuum-driven pump.

9. The system of claim 6 wherein said pump means includes a hydraulic pump.

10. The system of claims 8 or 9 wherein said pump is a constant flow impeller type pump.

11. The system of claims 8 or 9 wherein said pump means includes a reciprocating pump.

12. The system of claim 6 wherein said pump means includes a raceway for a peristaltic-type pump and means associated with said raceway for receiving the drive means of a peristaltic pump and creating a peristaltic action in said fluid circuit tubing disposed along said raceway; and, fluid circuit tubing disposed along said peristaltic pump raceway.

13. The system of claim 6 wherein said operator first input means includes a normally-open valve.

14. The system of claim 13 wherein said normally-open valve includes a push-button-operated, spring-return valve.

15. The system of claim 6 further including a filter placed in fluid communication with and in series with the means for egress from the irrigation site.

16. The apparatus of claim 15 wherein said filter means including means for connecting said filter means to a source of vacuum for evacuating any debris that may accumulate on the filter.

17. The system of claim 6 wherein said irrigation system is a closed system for recirculating said irrigation fluid.

18. The system of claim 6 wherein said pump means includes a pneumatic pump.

* * * * *